(12) United States Patent
Rich et al.

(10) Patent No.: US 7,299,134 B2
(45) Date of Patent: Nov. 20, 2007

(54) METHOD FOR CORRELATING GENE EXPRESSION PROFILES WITH PROTEIN EXPRESSION PROFILES

(75) Inventors: William E. Rich, Redwood Shores, CA (US); T. William Hutchens, Mountain View, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 10/076,967

(22) Filed: Feb. 15, 2002
(Under 37 CFR 1.47)

(65) Prior Publication Data

US 2003/0054367 A1    Mar. 20, 2003

Related U.S. Application Data

(60) Provisional application No. 60/269,772, filed on Feb. 16, 2001.

(51) Int. Cl.
*G06F 19/00* (2006.01)
*G01N 24/00* (2006.01)

(52) U.S. Cl. .......................... 702/19; 702/20; 436/173

(58) Field of Classification Search ................ 702/19, 702/20
See application file for complete search history.

(56) References Cited

FOREIGN PATENT DOCUMENTS

| WO | WO 00/22168 A1 | 4/2000 |
| WO | WO 00/29848 A1 | 5/2000 |
| WO | WO 01/57530 A1 | 8/2001 |

OTHER PUBLICATIONS

Huber. Nature (2003) vol. 4, pp. 74-80.*
Alizadeh et al. Nature (2000) vol. 403, pp. 503-511.*
Borman, S. "Genomics rises to drug discovery challenge," *C&EN* Apr. 19, 1999, pp. 59-68.
Chakravarti, D.N. "Application of genomics and proteomics for identification of bacterial gene products as potential vaccine candidates," *Vaccine* 2001, pp. 601-612, vol. 19.
Hancock, W. et al. "Report: Integrated genomic/proteomic analysis," *Analytical Chemistry News & Features* Nov. 1, 1999, pp. 742A-748A.
Nelson, P.S. et al. "Comprehensive analyses of prostate gene expression: Convergence of expressed sequence tag databases, transcript profiling and proteomics," *Electrophoresis* 2000, pp. 1823-1831, vol. 21.
Celis, J. E. et al., "Gene expression profiling: Monitoring transcription and translation products using DNA microarrays and proteomics." FEBS Lets., 480(1):2-16 (2000).
Dove, A., "Proteomics: Translating genomics into products?" Nat. Biotech., 17(3):233-36 (1999).
Gygi, S. P. et al., Correlation between protein and MRNA abundance in yeast.: Mol. Cell. Biol., 19:1720-30 (1999).
Pandey, A. and M. Mann, "Proteomics to study genes and genomes." Nature, 405(6788):837-46 (2000).
Shevchenko, A. et al., "Linking genome and proteome by mass spectrometry: Large-scale identification of yeast proteins from two dimensional gels." Proc. Natl. Acad. Sci. USA, 93(25):14440-45 (1996).
Griffin, T., et al. "Advances in Proteome Analysis by Mass Spectrometry," The Journal of Biological Chemistry, 2001, vol. 276, No. 49, pp. 45497-45500.
Aebersold, R., et al. "Mass spectrometry-based proteomics," Nature, 2003, vol. 422, pp. 198-207.
Huber, L. "Is proteins heading in the wrong direction," Molecular and Cell Biology, 2003, vol. 4, pp. 74-80.

* cited by examiner

*Primary Examiner*—Lori A. Clow
(74) *Attorney, Agent, or Firm*—Townsend and Townsend and Crew LLP

(57) ABSTRACT

The present invention relates to methods for correlating gene and protein expression in a cell.

26 Claims, No Drawings

METHOD FOR CORRELATING GENE EXPRESSION PROFILES WITH PROTEIN EXPRESSION PROFILES

CROSS-REFERENCES TO RELATED APPLICATIONS

The present application claims priority to U.S. Ser. No. 60/269,772, filed Feb. 16, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Genomics is the study of the collective set of genes (the genome) of a species, as well as study of the function and activity of those genes, in different cells and in the same cell, temporally, developmentally, and under varying environmental conditions. Differential gene function and activity plays a significant role in the development of a cell for a specialized activity in the body and the transformation of a cell from healthy into pathologic.

The expression of genetic information in a cell is carried out through the transcription of an intermediate molecule, mRNA. The cell translates expressed mRNAs into polypeptides, or proteins. Proteins carry out the majority of functions encoded by the genes. The study of the collective set of proteins (the proteome) of a species, and the activity and function of those proteins in a cell is the subject of a new field of biology called "proteomics."

Because the character of a cell depends on the genes expressed by the cell, gene expression profiling has become an important method in genomics. Gene expression profiling seeks to determine which genes are expressed in a cell and the level of their expression. Thus, the gene expression profile of a cell provides a "fingerprint" that is characteristic of the cell, indicating both the identity of the cell and its activity. Comparing the gene expression profiles of different cells is a process called "differential gene expression." This method can provide information about the genes that are responsible for the different phenotypes of cells. Genes that are differentially expressed in healthy and pathologic cells can function as diagnostic markers and are candidate targets for therapeutic intervention. Thus, obtaining accurate profiles of gene expression in different cell types is an important goal.

There are numerous methods presently used to generate gene expression profiles of a cell. These methods include traditional methods such as northern blots, RT-PCR, nuclease protection, differential display, cDNA fingerprinting, and subtractive hybridization, as well a newer techniques such as the generation of expressed sequence tag, or "EST" libraries and arrays, cDNA arrays, mRNA arrays, oligonucleotide arrays, and serial analysis of gene expression, or "SAGE" (see generally Lockhar & Winzeler, *Nature* 405:827-836 (2000); see also Velculescu et al., *Science* 270:484-487 (1995)).

In one example, nucleic acid arrays such as oligonucleotide arrays are used for expression profiling. These arrays are collections of specifically chosen oligonucleotides that are bound to a solid support at predetermined and addressable locations. In certain embodiments, these arrays comprise an oligonucleotide that specifically identifies each of the known genes in a genome. Messenger RNAs or cDNAs derived from a cell are applied to the array. Each mRNA or cDNA hybridizes with an oligonucleotide that corresponds to the particular gene from which it was transcribed. Because the identity and location of each immobilized oligonucleotide is predetermined, each hybridization event indicates that a particular gene has been expressed by the cell. One commercialized version of an oligonucleotide array is the GeneChip™ from Affymetrix. In yet another example of commercialized array methodology, beads coated with an array, or cells, are each attached to an optical sensor molecule. To provide an address, the beads are then drawn into wells at the end of fibers in a fiber optic bundle (see, e.g., Bead Array™ (Illumina)). In yet another example, arrays can be made from EST libraries. EST libraries are generated by reverse-transcribing the set of expressed mRNA in a cell. Frequently, the entire mRNA is not reverse transcribed, but a sufficient portion of it is to uniquely identify the gene from which the mRNA was expressed. The ESTs are sequenced and identified in a genomic database.

Despite the power of existing gene expression technologies, it is acknowledged that levels of mRNA transcription do not always correlate directly to levels of protein expression, for a number of reasons: (1) different mRNAs may be translated into polypeptides with different efficiencies; (2) an mRNA may be differentially spliced to produce different proteins in different cells; (3) expressed polypeptides may be degraded at different rates; and (4) polypeptides can be subject to post-translational modifications so that the same polypeptide can assume a different form or function in the same cell and in different cells. Thus, there is a need to correlate mRNA expression with protein expression (see, e.g., Hancock et al., *Anal. Chem. News & Features*, Nov. 1, 1999, page 742A-748A; Nelson et al., *Electrophoresis* 21:1823-1831 (2000)).

At the same time, current methods of protein expression profiling, such as mass spectrometry, 2D gel electrophoresis, and chromatography, may suffer from limitations in sensitivity and resolution (see, e.g., Pandey & Mann, *Nature* 405:837-846 (2000)). The present invention therefore address this issue by combining gene expression profiling and protein profiling to more quickly and accurately identify proteins of interest in a particular cell type. Gene expression profiling is used to select a candidate transcript or transcripts that are expressed in a cell. The transcripts are typically sequenced and used to deduce the amino acid sequence of the encoded protein. The amino acid sequence is then used to predict and identify physio-chemical characteristics of the protein encoded by transcript, e.g., molecular weight, isoelectric point, hydrophobicity, hydrophilicity, glycosylation, phosphorylation, epitope sequence, ligand binding sequence, charge at specified pH, or metal chelate binding. The physio-chemical characteristics are then employed to improve the sensitivity and resolution of protein profiling, thereby providing improved information about the proteins encoded by mRNA expressed in a particular cell type. This invention provides methods for making such a correlation and provides other advantages, as well.

SUMMARY OF THE INVENTION

The present invention therefore provides methods for correlating gene expression with protein expression. The methods involve performing gene expression profiling on a sample, selecting one or more expressed genes for further study, determining a physio-chemical property characteristic of the proteins encoded by these genes, and determining whether the proteins are expressed in the sample using the physio-chemical property as an identifier in a protein expression profile of the sample. In certain embodiments, the selected gene is differentially expressed in two cells or samples of interest, for example, a healthy cell and a pathologic cell, or two cells at different stages of a cell cycle, maturation, or differentiation pathway, or under different environmental conditions. In a preferred embodiment, the proteins are fractionated using mass spectrometry. In another preferred embodiment, the proteins are fractionated using SELDI (surface enhanced laser desorption ionization).

The methods of the invention are therefore useful in the identification of target proteins for drug discovery, and for the identification of diagnostic markers, for disease states such as cancer, e.g., prostate, breast, lung, bladder, ovarian, colon, brain and kidney; cancer metastasis; diabetes, both juvenile and late-onset; autoimmune disease such as rheumatoid arthritis and multiple sclerosis; heart disease, e.g., myocardial infarction, atherosclerosis, and cardiomyopathy; cerebrovascular disease, e.g., stroke; renal disease; lung disease, e.g., emphysema; viral infection, e.g., HIV, HCV, CMV, HPV, HBV; bacterial infection, e.g., *M. tuberculosis*, toxigenic *E. coli, Streptococcus sp., Staphylococcus sp.*; fungal infection; protozoal infection; e.g., malaria, schistosomiasis, Chagas disease. The methods of the present invention are also useful for investigating the expression products of different alleles, for, e.g., pharmacogenetic applications. The methods of the present invention are also useful for toxicology studies, and for investigating the effects of exposure of a cell to varying environmental conditions, such as radiation, e.g., UV radiation, heat, and cold.

BRIEF DESCRIPTION OF THE DRAWINGS

Not applicable.

DETAILED DESCRIPTION OF THE INVENTION

Introduction

The present invention provides methods that combine RNA and protein expression profiling, to identify genes and the proteins expressed in cells under different conditions, e.g., at different times in the cell cycle, under varying environmental conditions (such as ion influx or efflux; exposure to a toxin; drug; ligand; e.g., a hormone, a cytokine, or a chemokine; or a pathogen such as a virus, bacteria, protozoa, or fungus), under varying pathological conditions, such as cancer, at different times during maturation and differentiation, at different times during development of the organism, during responses such as inflammation, in different tissue types or organs, in different pathological conditions such as cancer or autoimmune disease, between individuals with different phenotypic traits, e.g., responders vs. non-responders to a particular pharmaceutical drug, etc. The methods of the present invention, e.g., allow one of skill in the art to identify a list of candidate genes expressed in a cell or biological sample, and then to further identify a subset of proteins of interest encoded by the genes of interest using the methods of the invention. The methods of the invention are also useful for combining information related to mRNA expression to expression and function of the protein encoded by the mRNA.

The invention therefore provides a method of correlating gene and protein expression in a cell, comprising the steps of obtaining a biological sample; generating a gene expression profile of the sample, thereby identifying one or more mRNAs expressed in the sample; predicting and identifying one or more physio-chemical properties of the polypeptides encoded by the RNAs; and identifying one or more polypeptides encoded by the mRNAs, the polypeptides comprising the physio-chemical property in the sample, by fractionating the polypeptides in the sample, thereby correlating gene and protein expression the in sample.

In one embodiment, the step of generating the gene expression profile comprises identifying expressed mRNA with an EST array, an mRNA array, or an oligonucleotide array.

In another embodiment, the step of identifying the polypeptide comprises fractionating polypeptides in the sample using 2-D electrophoresis, chromatography, mass spectrometry, or SELDI.

In another embodiment, the physiochemical characteristic is selected from the group consisting of amino acid sequence, molecular weight, iso-electric point, hydrophobicity, hydrophilicity, charge (e.g., isoelectric point), glycosylation, phosphorylation, epitope sequence or antibody binding, ligand binding, dye binding, and metal chelate binding. In another embodiment, the step of identifying a physiochemical characteristic comprises predicting the masses of proteolytic fragments generated by the encoded polypeptide upon degradation of the encoded polypeptide by a selected proteolytic agent, and the step of identifying a polypeptide comprises subjecting polypeptides in the sample to degradation by the agent and identifying actual proteolytic fragments in the sample having masses that correspond to the masses of the predicted fragments.

In another embodiment, the sample comprises a human cell. In another embodiment, the sample comprises a cell lysate from a normal or healthy cell. In another embodiment, the sample comprises a cell lysate from a pathological cell. In another embodiment, the sample comprises a cell lysate from a cell that has been contacted with a toxic compound. In another embodiment, the biological sample comprises a cell lysate from a cell of a subject who respond to a drug treatment or a subject who does not respond to a drug treatment.

In one embodiment, the sample is tissue from a human. In another embodiment, the mRNA is differentially expressed in two biological samples. In another embodiment, the two biological samples are a normal or healthy cell and a pathological cell, e.g., a cancer cell. In another embodiment, the two biological samples are derived from a healthy cell and a cell exposed to a toxic compound.

In another embodiment, the sample comprises a biopsy; cultured cells, e.g., transformed cells, cells from a cell line, an explant, or a primary culture; blood, serum, sputum, stool, or urine.

In a preferred aspect of the invention, the method comprises the steps of: obtaining a biological sample; generating a gene expression profile of the cell using an nucleic acid array, thereby identifying one or more mRNAs expressed in the cell; identifying one or more physio-chemical properties of a polypeptide encoded by the mRNA; and identifying a polypeptide comprising the physio-chemical property by fractionating the polypeptides in the sample with mass spectrometry; thereby correlating gene and protein expression in the cell.

In a preferred aspect of the invention, the method comprises the steps of: obtaining a biological sample comprising a cell; generating a gene expression profile of the cell using an oligonucleotide array, thereby identifying one or more mRNAs expressed in the cell; identifying one or more physio-chemical properties of a polypeptide encoded by the mRNA; and identifying a polypeptide comprising the physio-chemical property by fractionating the polypeptides in the sample with SELDI, wherein SELDI comprises fractionating by affinity retention on solid phase-bound adsorbent followed by fractionating retained proteins from the solid phase by gas phase ion spectrometry; thereby correlating gene and protein expression in the cell.

In one embodiment, the method comprises using more than one technique to identify either mRNA or proteins expressed in the sample.

In one embodiment, the genomics arrays compare expression of housekeeping genes with other tissue specific genes. In one embodiment, the genomics arrays compare differential levels of gene expression. In one embodiment, the genomics arrays compare similar levels of gene expression.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Biological sample" refers to a sample derived from a virus, cell, tissue, organ or organism (either eukaryotic or prokaryotic) including, without limitation, cell, tissue or organ lysates or homogenates, or body fluid samples, such as blood, urine, sputum, or cerebrospinal fluid. Such samples include, but are not limited to, tissue isolated from humans, or explants, primary, and transformed cell cultures derived therefrom. Biological samples may also include sections of tissues such as frozen sections taken for histologic purposes. A biological sample can be obtained from a eukaryotic organism such as fungi, plants, insects, protozoa, birds, fish, reptiles, and preferably a mammal such as rat, mice, cow, dog, guinea pig, or rabbit, and most preferably a primate such as chimpanzees or humans.

"Biopolymer" refers to a polymer of biological origin, e.g., polypeptides, polynucleotides, polysaccharides or polyglycerides (e.g., di- or tri-glycerides).

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

"Polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules (see, e.g., Fahrlander & Klausner, *Biotechnology* 6:1165 (1988)). Quantitation of the signal is achieved by, e.g., scintillation counting, densitometry, or flow cytometry.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from open reading frames that flank the gene and encode proteins other than protein encoded by the gene. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Purify" or "purification" means removing at least one contaminant from the composition to be purified. Purification does not require that the purified compound be 100% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well. Appropriate unicellular hosts include any of those routinely used in expressing eukaryotic or mammalian polynucleotides, including, for example, prokaryotes, such as E. coli; and eukaryotes, including for example, fungi, such as yeast; and mammalian cells, including insect cells (e.g., Sf9) and animal cells such as CHO, R1.1, B-W, L-M, African Green Monkey Kidney cells (e.g. COS 1, COS 7, BSC 1, BSC 40 and BMT 10) and cultured human cells.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min.

"Plurality" means at least two.

A "ligand" is a compound that specifically binds to a target molecule.

A "receptor" is compound that specifically binds to a ligand.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. This term also encompasses, e.g., polyclonal, monoclonal, single-chain, humanized, chimeric antibodies, and fragments thereof.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (*see Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

"Agent" refers to a chemical compound, a mixture of chemical compounds, a sample of undetermined composition, a combinatorial small molecule array, a biological macromolecule, a bacteriophage peptide display library, a bacteriophage antibody (e.g., scFv) display library, a polysome peptide display library, or an extract made from biological materials such as bacteria, plants, fungi, or animal cells or tissues. Suitable techniques involve selection of libraries of recombinant antibodies in phage or similar vectors (see, e.g., Huse et al., *Science* 246:1275-1281 (1989); and Ward et al., *Nature* 341:544-546 (1989)). The protocol described by Huse is rendered more efficient in combination with phage display technology (see, e.g., WO 91/17271 and WO 92/01047.

"Expression control sequence" refers to a nucleotide sequence in a polynucleotide that regulates the expression (transcription and/or translation) of a nucleotide sequence operatively linked to it. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible, repressible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Energy absorbing molecule" refers to refers to a molecule that absorbs energy from an energy source in a desorption spectrometer thereby enabling desorption of analyte from a probe surface. Energy absorbing molecules used in MALDI are frequently referred to as "matrix." Cinnamic acid derivatives (such as alpha-4-cyano-4-hydroxy-cinammic acid), cinnapinic acid and dihydroxybenzoic acid are frequently used as energy absorbing molecules in laser desorption of bioorganic molecules.

"Probe" refers to a device that is removably insertable into a gas phase ion spectrometer (e.g., a mass spectrometer) that contains a substrate having a surface adapted for the presentation of an analyte for detection. The probes may be modified as a result of the analysis and may be disposable.

"Gas phase ion spectrometer" refers to an apparatus that measures a parameter which can be translated into mass-to-charge ratios of ions formed when a sample is volatilized and ionized. Generally ions created by laser desorption/ionization bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector. Examples of mass spectrometers are time-of-flight, magnetic sector, quadrapole filter, ion trap, ion cyclotron resonance and hybrids of these.

"Laser desorption mass spectrometer" refers to a mass spectrometer which uses laser as means to desorb, volatilize, and ionize an analyte.

"Mass spectrometry" refers to the analysis of sample by a mass spectrometer.

A "quadrupole time-of-flight mass spectrometer" refers to a mass spectrometer that contains a collisional damping interface that cools the ions formed by the energy source before the ions enter a quadrupole Q. The quadrupole time-of-flight mass spectrophotometer can also contain a collision cell.

"Analyte" refers to a component of a sample which is desirably retained and detected. The term can refer to a single component or a set of components in the sample.

"Adsorbent" refers to any material capable of adsorbing an analyte. The term "adsorbent" is used herein to refer both to a single material ("monoplex adsorbent") (e.g., a compound or finctional group) to which the analyte is exposed, and to a plurality of different materials ("multiplex adsorbent") to which a sample is exposed. The adsorbent materials in a multiplex adsorbent are referred to as "adsorbent species." For example, an addressable location on a substrate can comprise a multiplex adsorbent characterized by many different adsorbent species (e.g., anion exchange materials, metal chelators, or antibodies), having different binding characteristics.

"Adsorb" refers to the detectable binding between an absorbent and an analyte either before or after washing with an eluant (selectivity threshold modifier).

"Substrate" refers to a solid phase to which an adsorbent is attached or deposited.

"Binding characteristic" refers to a chemical and physical feature that dictates the attraction of an adsorbent for an analyte. Two adsorbents have different binding characteristics if, under the same elution conditions, the adsorbents bind the same analyte with different degrees of affinity. Binding characteristics include, for example, degree of salt-promoted interaction, degree of hydrophobic interaction, degree of hydrophilic interaction, degree of electrostatic interaction, and others described herein.

"Binding conditions" refer to the binding characteristics to which an analyte is exposed.

"Eluant" refers to an agent, typically a solution, that is used to mediate adsorption of an analyte to an adsorbent. Eluants also are referred to as "selectivity threshold modifiers."

"Elution characteristic" refers to a feature that dictates the ability of a particular eluant (selectivity threshold modifier) to mediate adsorption between an analyte and an absorbent. Two eluants have different elution characteristics if, when put in contact with an analyte and adsorbent, the degree of affinity of the analyte for the adsorbent differs. Elution characteristics include, for example, pH, ionic strength, modification of water structure, detergent strength, modification of hydrophobic interactions, and others described herein.

"Elution conditions" refer to the elution characteristics to which an analyte is exposed.

"Selectivity characteristic" refers to a feature of the combination of an adsorbent having particular binding characteristics and an eluant having particular elution characteristics that dictate the specificity with which the analyte is retained to the adsorbent after washing with the eluant.

"Selectivity conditions" refer to the selectivity characteristics to which an analyte is exposed.

"Basis for attraction" refers to the chemical and/or physio-chemical properties which cause one molecule to be attracted to another.

"Strength of attraction" refers to the intensity of the attraction of one molecule for another (also known as affinity).

"Resolve," "resolution," or "resolution of analyte" refers to the detection of at least one analyte in a sample. Resolution includes the detection of a plurality of analytes in a sample by separation and subsequent differential detection. Resolution does not require the complete separation of an analyte from all other analytes in a mixture. Rather, any separation that allows the distinction between at least two analytes suffices.

"High information resolution" refers to resolution of an analyte in a manner that permits not only detection of the analyte, but also at least one physio-chemical property of the analyte to be evaluated, e.g., molecular mass.

"Desorption spectrometry" refers to a method of detecting an analyte in which the analyte is exposed to energy which desorbs the analyte from a stationary phase into a gas phase, and the desorbed analyte or a distinguishable portion of it is directly detected by a detector, without an intermediate step of capturing the analyte on a second stationary phase.

"Detect" refers to identifying the presence, absence or amount of the object to be detected.

"Retention" refers to an adsorption of an analyte by an adsorbent after washing with an eluant.

"Retention data" refers to data indicating the detection (optionally including detecting mass) of an analyte retained under a particular selectivity condition.

"Retention map" refers to a value set specifying retention data for an analyte retained under a plurality of selectivity conditions.

"Recognition profile" refers to a value set specifying relative retention of an analyte under a plurality of selectivity conditions.

"Complex" refers to analytes formed by the union of 2 or more analytes. "Fragment" refers to the products of the chemical, enzymatic, or physical breakdown of an analyte. Fragments may be in a neutral or ionic state.

"Differential expression" refers to a detectable difference in the qualitative or quantitative presence of an analyte.

"Gene expression profile" refers to the identification of at least one mRNA expressed in a biological sample.

"Physio-chemical property" refers to a physical or chemical property of a molecule that is characteristic the molecule. Physio-chemical properties of proteins include, without limitation, amino acid sequence, molecular weight, isoelectric point, hydrophobicity, hydrophilicity, glycosylation, phosphorylation, epitope sequence, ligand binding sequence, charge at a specified pH (isoelectric point), dye binding, and metal chelate binding. A physiochemical property is used, e.g., as an identifier or means of fractionation or isolation in a protein profile. For example, an amino acid sequence feature such as a hexa-histidine sequence, ligand binding motif or sequence, domain, protease cleavage site, metal chelate binding site, or epitope, can be used to fractionate, isolate or identify a polypeptide comprising such a sequence. In another example, phosphorylated polypeptide can be fractionated, isolated or identified via interaction with a corresponding kinase or phosphorylase, or by a colorimetric enzyme reaction, or by an antibody that binds to the phosphorylated portion of the polypeptide. Similarly, a glycosylated polypeptide can be fractionated, isolated, or identified via an interaction with a binding partner, or an antibody that binds to the glycosylated portion of the polypeptide, or by an antibody that recognizes the carbohydrate, or by a lectin, or enzymatically. In another example, buffers and solutions of varying pH, or anionic or cationic resins, can be used to fractionate, isolate or identify polypeptides according to their charge at a given pH, or their pI or isoelectric point. In another example, buffers, solutions, and resins of varying hydrophilicity can be used to fractionate, isolate, or identify polypeptides based on their hydrophobicity or hydrophilicity. In another example, mass or molecular weight, or the mass or molecular weight of proteolytic fragments of the polypeptide can be used to isolate, identify, or fractionate the polypeptide.

"Nucleic acid array" refers to an array of addressable locations (i.e., a location characterized by a distinctive, interrogatable address), each addressable location comprising a characteristic nucleic acid attached thereto. A nucleic acid can be any nucleic acid as defined herein, e.g., a naturally occurring or synthetic nucleic acid, e.g., an oligonucleotide or polynucleotide. In an oligonucleotide array, the nucleic acid is an oligonucleotide (e.g., corresponding to an exon, EST, or a portion of a gene, transcript, or cDNA); in an EST array the nucleic acid is an EST or portion thereof; in an mRNA array the nucleic acid is an mRNA or portion thereof, or a corresponding cDNA. An oligonucleotide can be from 4, 6, 8, 10, or 12 nucleotides or longer in length, often 10, 30, 40, or 50 nucleotides in length, up to about 100 nucleotides in length.

Gene Expression Profiling

A first step in the methods of the invention is performing gene expression profiling of a sample of interest. Gene expression profiling refers to examining expression of one or more RNAs in a cell, preferably mRNA. Often at least or up to 10, 100, 100, 10,000 or more different mRNAs are examined in a single experiment. In one embodiment, differential profiling (comparison with another cell, e.g., that has a different phenotype, or is at a different temporal or developmental stage, or has been exposed to different environmental conditions, e.g., physical or chemical conditions, etc.) provides useful information about the cell of interest, e.g., genes that are preferentially or selectively expressed in a given cell type. Often, a gene of interest is highly expressed in one cell but not another. In other embodiments, the gene of interest has a similar expression pattern in different cells. In other embodiments, the gene of interest has low expression in one cell as compared to another.

Methods for examining gene expression, often but not always hybridization based, include, e.g., northern blots; dot blots; primer extension; nuclease protection; subtractive hybridization and isolation of non-duplexed molecules using, e.g., hydroxyapatite; solution hybridization; filter hybridization; amplification techniques such as RT-PCR and other PCR-related techniques such as differential display, LCR, AFLP, RAP, etc. (see, e.g., U.S. Pat. Nos. 4,683,195 and 4,683,202; *PCR Protocols: A Guide to Methods and Applications* (Innis et al., eds, 1990); Liang & Pardee, *Science* 257:967-971 (1992); Hubank & Schatz, *Nuc. Acids Res.* 22:5640-5648 (1994); Perucho et al., *Methods Enzymol.* 254:275-290 (1995)), fingerprinting, e.g., with restriction endonucleases (Ivanova et al., *Nuc. Acids. Res.* 23:2954-2958 (1995); Kato, *Nuc. Acids Res.* 23:3685-3690 (1995); and Shimkets et al., *Nature Biotechnology* 17:798-803, see also U.S. Pat. No. 5,871,697)); and the use of structure specific endonucleases (see, e.g., De Francesco, *The Scientist* 12:16 (1998)). mRNA expression can also be analyzed using mass spectrometry techniques (e.g., MALDI or SELDI), liquid chromatography, and capillary gel electrophoresis, as described below.

For a general description of these techniques, see also Sambrook et al., *Molecular Cloning, A Laboratory Manual* (2nd ed. 1989), see, e.g., pages 7.37-7.39, 7.53-7.54, 7.58-7.66, and 7.71-7.79; Kriegler, *Gene Transfer and Expression: A Laboratory Manual* (1990); and *Current Protocols in Molecular Biology* (Ausubel et al., eds., 1994).

Techniques have been developed that expedite expression analysis and sequencing of large numbers of nucleic acids samples. For example, nucleic acid arrays have been developed for high density and high throughput expression analysis (see, e.g., Granjeuad et al., *BioEssays* 21:781-790 (1999); Lockhart & Winzeler, *Nature* 405:827-836 (2000)). Nucleic acid arrays refer to large numbers (e.g., hundreds, thousands, tens of thousands, or more) of nucleic acid probes bound to solid substrates, such as nylon, glass, or silicon wafers (see, e.g., Fodor et al., *Science* 251:767-773 (1991); Brown & Botstein, *Nature Genet.* 21:33-37 (1999); Eberwine, *Biotechniques* 20:584-591 (1996)). A single array can contain, e.g., probes corresponding to an entire genome, or to all genes expressed by the genome. The probes on the array can be DNA oligonucleotide arrays (e.g., GeneChip™, see, e.g., Lipshutz et al., *Nat. Genet.* 21:20-24 (1999)), mRNA arrays, cDNA arrays, EST arrays, or optically encoded arrays on fiber optic bundles (e.g., BeadArray™). The samples applied to the arrays for expression analysis can be, e.g., PCR products, cDNA, mRNA, etc.

Additional techniques for rapid gene sequencing and analysis of gene expression include, e.g., SAGE (serial analysis of gene expression). For SAGE, a short sequence tag (typically about 10-14 bp) contains sufficient information to uniquely identify a transcript. These sequence tags can be linked together to form long serial molecules that can be cloned and sequenced. Quantitation of the number of times a particular tag is observed proves the expression level of the corresponding transcript (see, e.g., Velculescu et al., *Science* 270:484-487 (1995); Velculescu et al., *Cell* 88 (1997); and de Waard et al., *Gene* 226:1-8 (1999)).

Physio-chemical Properties

As described herein, each of these techniques can be used, alone or in combination, to identify a candidate gene or set of candidate genes of interest that are expressed in a cell. Transcripts of interest are identified and isolated using techniques known to those of skill in the art. The transcript so identified is sequenced and, using the encoded amino acid sequence information, is analyzed for physiochemical characteristics, such as molecular weight, iso-electric point, hydrophobicity, hydrophilicity, glycosylation, phosphorylation, epitope sequence, protease fragmentation, ligand binding sequence, charge at a specified pH, and metal chelate binding. Often, bioinformatics and sequence databases can be used to identify a function of the protein encoded by the transcript. Genes of interest include, e.g., ion channels, receptors, e.g., G protein coupled receptors, cytokines, chemokines, signal transduction proteins, housekeeping proteins, cell cycle regulation proteins, transcription factors, zinc finger proteins, chromatin remodeling proteins, etc.

The physio-chemical properties so identified are tools for correlating the level of expression of a transcript with the level of expression of the protein encoded by the transcript. Using the protein analysis tools described below, one or more of the physio-chemical characteristics of the protein can be used fractionate the proteins of interest, while reducing background and increasing sensitivity of protein detection. In this manner, a candidate transcript or transcripts of interest can be further correlated with the level of expression of the encoded protein in a cell. This information can be used to select a subset of transcripts and proteins for use in, e.g., diagnostic and therapeutic applications.

Protein Fractionation Analysis of Samples

Polypeptides in the sample are then fractionated based on at least one physio-chemical property of the polypeptide encoded by the identified expressed mRNA. For example, the identity of the polypeptide will indicate several predicted physio-chemical characteristics of the polypeptide. Amino acid sequence will provide a predicted molecular mass of the protein. The amino acid sequence also can be used to predict the isoelectric point of the polypeptide, whether the polypeptide is hydrophilic or hydrophobic and whether the polypeptide has metal chelate binding ability. Amino acid sequence also can indicate whether the polypeptide includes glycosylation or phosphorylation sites. Post-translational modifications of the polypeptide will be reflected in changes to molecular weight. Amino acid sequence also can identify epitopes which, in turn, may be targets for antibody binding. An exact measurement of the physiochemical property is not necessary; it is sufficient to obtain some information so that upon fractionation into a plurality of aliquots based on that characteristic, the polypeptide is expected to be preferentially fractionated among the aliquots.

The polypeptides in the sample are then fractionated based on a physiochemical characteristic of the polypeptide. A most useful method of separation is molecular weight, as there are many useful methods to separate proteins based on this characteristic including, for example, SDS gel electrophoresis and gas phase ion spectrometry, e.g., mass spectrometry. Another useful physiochemical characteristic is isoelectric point. Isoelectric focusing, affinity chromatography and solid phase extraction on an ion exchange resin will fractionate proteins in a sample based on this property.

Methods of fractionating proteins are used to examine the level of expression of a selected protein in a cell. As described above, the use of one or more elected physiochemical characteristics can enhance the sensitivity of fractionation and reduce background. The techniques described herein can be used to examine one or more proteins expressed in a cell, up to tens, hundreds, thousands, or tens of thousands of proteins. Any one technique or a combination of techniques can be used to fractionate the proteins, based on one or more physio-chemical property. Methods of fractionation include, e.g., two dimensional gels; capillary gel electrophoresis; mass spectrometry, e.g., MALDI, SELDI; ICAT (isotope coded affinity tag, see, e.g., Mann, *Nature Biotechnology* 17:954-955 (1999); Gygi et al., *Nature Biotechnology* 17:994-999 (1999)); chromatography, e.g., gel-filtration, ion-exchange, affinity, immunoaffinity, and metal chelate chromatography, HPLC, e.g., reversed phase, ion-exchange, and size exclusion HPLC; western blotting; immunohistochemistry techniques such as ELISA and in situ screening with antibodies, etc (see, e.g., Blackstock & Weir, *Trends in Biotech.* 17:121-127 (1999); Dutt & Lee, *Biochemical Engineering*, pages 176-179 (April 2000); Page et al., *Drug Discovery Today* 4:55-62 (1999); Wang & Hewick, Drug Discovery Today 4:129-133 (1999); Regnier et al., *Trends in Biotech.* 17:101-106 (1999); and Pandey & Mann, *Nature* 405:837-846 (2000)). The proteins of interest are identified and isolated using techniques known to those of skill in the art.

For a general description of these techniques, see also Sambrook et al., *Molecular Cloning, A Laboratory Manual* (2nd ed. 1989); and *Current Protocols in Molecular Biology* (Ausubel et al., eds., 1994).

In one embodiment, two-dimensional electrophoresis can be used to fractionate the proteins of the invention. This technique fractionates proteins based on the physio-chemical characteristics of pI and molecular weight. 2d gel electrophoresis and the techniques described herein can be used alone, or in combination with other techniques such as mass spectrometry, e.g., MALDI and SELDI, described herein below.

In another embodiment, described below, MALDI is a mass spectrometry technique that fractionates proteins based on mass, and is often combined with size and or affinity chromatography techniques to increase resolution.

In another embodiment, described below, SELDI is a mass spectrometry technique that couples affinity fractionation with mass spectrometry. An affinity matrix or probe based on, e.g., pI (ion exchange resin and wash), antibody binding, glycosylation, phosphorylation, histidine residues, etc. is used in SELDI, in combination with mass spectrometry, to identify proteins with high resolution, accuracy, and sensitivity. When using this technique, an affinity matrix that enriches for the candidate polypeptides can be determined, based on the physio-chemical characteristics of the protein encoded by the transcript.

Mass Spectrometry Analysis of Samples

Introduction

The polypeptides of the invention or fragments thereof can be analyzed using mass spectrometry methods. This method fractionates the polypeptides based on mass. In certain embodiments gas phase ion spectrophotometer is used. In other embodiments, laser-desorption/ionization mass spectrometry is used to analyze the sample on the substrate-bound adsorbent.

Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). Mass spectrometers utilizing laser desorption/ionization mass spectrometry can be further coupled to a quadrupole time-of-flight mass spectrometer. In MALDI, the analyte, which may contain biological molecules, is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with affinity reagents that selectively bind the analyte. In another variant, the surface is derivatized with energy absorbing molecules that are not desorbed when struck with the laser. In another variant, the surface is derivatized with molecules that bind the analyte and that contain a photolytic bond that is broken upon application of the laser. In each of these methods, the derivatizing agent generally is localized to a specific location on the substrate surface where the sample is applied. See, e.g., U.S. Pat. Nos. 5,719,060 and 5,6020208 (Hutchens & Yip) and WO 98/59360, WO 98/59361, and WO 98/59362 (Hutchens & Yip). The two methods can be combined by, for example, using a SELDI affinity surface to capture an analyte and adding matrix-containing liquid to the captured analyte to provide the energy absorbing material.

In certain embodiments, the laser desorption/ionization mass spectrophotometer is further coupled to a quadrupole time-of-flight mass spectrometer QqTOF MS (see, e.g., Krutchinsky et al., WO 99/38185). Methods such as MALDI-QqTOFMS (Krutchinsky et al., WO 99/38185; Shevchenko et al. (2000) *Anal. Chem.* 72: 2132-2141), ESI-QqTOF MS (Figeys et al. (1998) *Rapid Comm'ns. Mass Spec.* 12-1435-144) and chip capillary electrophoresis (chip-CE)-QqTOF MS(Li et al. (2000) *Anal. Chem.* 72: 599-609) have been described previously.

In one embodiment, a mass spectrometer is used to fractionate protein samples of the invention. In a typical mass spectrometer, a substrate containing a polypeptide analyte is introduced into an inlet system of the mass spectrometer. The analyte is then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector.

The detector then translates information of the detected ions into mass-to-charge ratios. Detection of the presence of a marker or other substances will typically involve detection of signal intensity. This, in turn, can reflect the quantity and character of a polypeptide bound to the substrate. The mass spectrometers and their techniques are well known to those of skill in the art. Any person skilled in the art understands, any of the components of a mass spectrometer (e.g., desorption source, mass analyzer, detect, etc.) can be combined with other suitable components described herein or those known in the art. For additional information regarding mass spectrometers, see, e.g., *Principles of Instrumental Analysis*, $3^{rd}$ ed., Skoog, Saunders College Publishing, Philadelphia, 1985; and *Kirk-Othmer Encyclopedia of Chemical Technology*, $4^{th}$ ed. Vol. 15 (John Wiley & Sons, New York 1995), pp. 1071-1094.

In one embodiment, a laser desorption time-of-flight mass spectrometer is used with the substrate of the present invention. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

Retentate chromatography is a method for the multidimensional resolution of analytes in a sample. The method involves (1) selectively adsorbing analytes from a sample to a substrate under a plurality of different adsorbent/eluant combinations ("selectivity conditions") and (2) detecting the retention of adsorbed analytes by desorption spectrometry. Each selectivity condition provides a first dimension of separation, separating adsorbed analytes from those that are not adsorbed. Desorption mass spectrometry provides a second dimension of separation, separating adsorbed analytes from each other according to mass. Because retentate chromatography involves using a plurality of different selectivity conditions, many dimensions of separation are achieved. The relative adsorption of one or more analytes under the two selectivity conditions also can be determined. This multidimensional separation provides both resolution of the analytes and their characterization.

Further, the analytes thus separated remain docked in a retentate map that is amenable to further manipulation to examine, for example, analyte structure and/or function. Also, the docked analytes can, themselves, be used as adsorbents to dock other analytes exposed to the substrate. In sum, the present invention provides a rapid, multidimensional and high information resolution of analytes.

The method can take several forms. In one embodiment, the analyte is adsorbed to two different adsorbents at two physically different locations and each adsorbent is washed with the same eluant (selectivity threshold modifier). In another embodiment, the analyte is adsorbed to the same adsorbent at two physically different locations and washed with two different eluants. In another embodiment, the analyte is adsorbed to two different adsorbents in physically different locations and washed with two different eluants. In another embodiment, the analyte is adsorbed to an adsorbent and washed with a first eluant, and retention is detected; then, the adsorbed analyte is washed with a second, different eluant, and subsequent retention is detected.

Methods Of Performing Retentate Chromatography

Retentate chromatography is a particularly useful method for fractionating polypeptides in a sample. According to this method, the polypeptides are fractionated on a solid phase adsorbent which binds polypeptides based on particular physio-chemical properties. Unbound polypeptides are washed away. Then the retained polypeptides are further fractionated by mass spectrometry, thereby providing fractionation based on at least two physio-chemical properties.

Exposing the Analyte to Selectivity Conditions

Substrate preparation: In performing retentate chromatography an analyte that is retained by an adsorbent is presented to an energy source on a substrate. A sample containing the analyte may be contacted to the adsorbent before or after the adsorbent is affixed to the substrate that will serve to present the analyte to the desorption means. For contacting purposes, the adsorbent may be in liquid form or solid form (i.e., on a substrate or solid phase). Specifically, the adsorbent may be in the form of a solution, suspension, dispersion, water-in-oil emulsion, oil-in-water emulsion, or microemulsion. When the adsorbent is provided in the form of a suspension, dispersion, emulsion or microemulsion, a suitable surfactant may also be present. In this embodiment, the sample may be contacted with the adsorbent by admixing a liquid sample with the liquid adsorbent. Alternatively, the sample may be provided on a solid support and contacting will be accomplished by bathing, soaking, or dipping the sample-containing solid support in the liquid adsorbent. In addition, the sample may be contacted by spraying or washing over the solid support with the liquid adsorbent. In this embodiment, different adsorbents may be provided in different containers.

In one embodiment, the adsorbent is provided on a substrate. The substrate can be any material which is capable of binding or holding the adsorbent. Typically, the substrate is comprised of glass; ceramic; electrically conducting polymers (e.g. carbonized PEEK); TEFLON® coated materials; organic polymers; native biopolymers; metals (e.g., nickel, brass, steel or aluminum); films; porous and non-porous beads of cross-linked polymers (e.g., agarose, cellulose or dextran); other insoluble polymers; or combinations thereof.

In one embodiment, the substrate takes the form of a probe or a sample presenting means that is inserted into a desorption detector. For example, referring to FIG. 1, the substrate can take the form of a strip. The adsorbent can be attached to the substrate in the form of a linear array of spots, each of which can be exposed to the analyte. Several strips can be joined together so that the plurality of adsorbents form an array 30 having discrete spots in defined rows. The substrate also can be in the form of a plate having an array of horizontal and vertical rows of adsorbents which form a regular geometric pattern such as a square, rectangle or circle.

Probes can be produced as follows. The substrate can be any solid material, for example, stainless steel, aluminum or a silicon wafer. A metal substrate can then be coated with a material that allows derivitization of the surface. For example a metal surface can be coated with silicon oxide, titanium oxide or gold.

The surface is then derivatized with a bifunctional linker. The linker includes at one end a functional group that can covalently bind with a functional group on the surface. Thus the functional group can be an inorganic oxide or a sulfhydryl group for gold. The other end of the linker generally has an amino functionality. Useful bifunctional linkers include aminopropyl triethoxysilane or aminoethyl disulfide.

Once bound to the surface, the linkers are further derivatized with groups that function as the adsorbent. Generally the adsorbent is added to addressable locations on the probe. In one type of probe spots of about 3 mm in diameter are arrange in an orthogonal array. The adsorbents can, themselves, be part of bifunctional molecules containing a group reactive with the available amino group and the functional group that acts as the adsorbent. Functional groups include, for example, normal phase (silicon oxide), reverse phase (C18 aliphatic hydrocarbon), quaternary amine and sulphonate. Also, the surface can be further derivatized with other bifunctional molecules such as carbodiimide and N-hydroxysuccinimide, creating a pre-activated blank. These blanks can be functionalized with bioorganic adsorbents (e.g., nucleic acids, antibodies and other protein ligands). Biopolymers can bind the functional groups on the blanks through amine residues or sulfhydryl residues. In one embodiment, the adsorbents are bound to cross-linked polymers (e.g., films) that are themselves bound to the surface of the probe through the available functional groups. Such polymers include, for example, cellulose, dextran, carboxymethyl dextran, polyacrylamide and mixtures of these. Probes with attached adsorbents are ready for use.

In another embodiment, the adsorbent is attached to a first substrate to provide a solid phase, such as a polymeric or glass bead, which is subsequently positioned on a second substrate which functions as the means for presenting the sample to the desorbing energy of the desorption detector. For example, the second substrate can be in the form a plate having a series of wells at predetermined addressable locations. The wells can function as containers for a first substrate derivatized with the adsorbent, e.g., polymeric beads derivatized with the adsorbent. One advantage of this embodiment is that the analyte can be adsorbed to the first substrate in one physical context, and transferred to the sample presenting substrate for analysis by desorption spectrometry.

Typically, the substrate is adapted for use with the detectors employed in the methods of the present invention for detecting the analyte bound to and retained by the adsorbent. In one embodiment, the substrate is removably insertable into a desorption detector where an energy source can strike the spot and desorb the analyte. The substrate can be suitable for mounting in a horizontally and/or vertically translatable carriage that horizontally and/or vertically moves the substrate to successively position each predetermined addressable location of adsorbent in a path for interrogation by the energy source and detection of the analyte bound thereto. The substrate can be in the form of a conventional mass spectrometry probe The strips, plates, or probes of substrate can be produced using conventional techniques. Thereafter, the adsorbent can be directly or indirectly coupled, fitted, or deposited on the substrate prior to contacting with the sample containing the analyte. The adsorbent may be directly or indirectly coupled to the substrate by any suitable means of attachment or immobilization. For example, the adsorbent can be directly coupled to the substrate by derivatizing the substrate with the adsorbent to directly bind the adsorbent to the substrate through covalent or non-covalent bonding.

Attachment of the adsorbent to the substrate can be accomplished through a variety of mechanisms. The substrate can be derivatized with a fully prepared adsorbent molecule by attaching the previously prepared adsorbent molecule to the substrate. Alternatively, the adsorbent can be formed on the substrate by attaching a precursor molecule to the substrate and subsequently adding additional precursor molecules to the growing chain bound to the substrate by the first precursor molecule. This mechanism of building the adsorbent on the substrate is particularly useful when the adsorbent is a polymer, particularly a biopolymer such as a DNA or RNA molecule. A biopolymer adsorbent can be provided by successively adding bases to a first base attached to the substrate using methods known in the art of oligonucleotide chip technology. See, e.g., U.S. Pat. No. 5,445,934 (Fodor et al.).

As can be seen from FIG. 2, as few as two and as many as 10, 100, 1000, 10,000 or more adsorbents can be coupled to a single substrate. The size of the adsorbent site may be varied, depending on experimental design and purpose. However, it need not be larger than the diameter of the impinging energy source (e.g., laser spot diameter). The spots can continue the same or different adsorbents. In some cases, it is advantageous to provide the same adsorbent at multiple locations on the substrate to permit evaluation against a plurality of different eluants or so that the bound analyte can be preserved for future use or reference, perhaps in secondary processing. By providing a substrate with a plurality of different adsorbents, it is possible to utilize the plurality of binding characteristics provided by the combination of different adsorbents with respect to a single sample and thereby bind and detect a wider variety of different analytes. The use of a plurality of different adsorbents on a substrate for evaluation of a single sample is essentially equivalent to concurrently conducting multiple chromatographic experiments, each with a different chromatography column, but the present method has the advantage of requiring only a single system.

When the substrate includes a plurality of adsorbents, it is particularly useful to provide the adsorbents in predetermined addressable locations. By providing the adsorbents in predetermined addressable locations, it is possible to wash an adsorbent at a first predetermined addressable location with a first eluant and to wash an adsorbent at a second predetermined addressable location with a second eluant. In this manner, the binding characteristics of a single adsorbent for the analyte can be evaluated in the presence of multiple eluants which each selectively modify the binding characteristics of the adsorbent in a different way. The addressable locations can be arranged in any pattern, but preferably in regular patters, such as lines, orthogonal arrays, or regular curves, such as circles. Similarly, when the substrate includes a plurality of different adsorbents, it is possible to evaluate a single eluant with respect to each different adsorbent in order to evaluate the binding characteristics of a given adsorbent in the presence of the eluant. It is also possible to evaluate the binding characteristics of different adsorbents in the presence of different eluants.

Incremental or Gradient Adsorbent Surfaces: A series of adsorbents having different binding characteristics can be provided by synthesizing a plurality of different polymeric adsorbents on the substrate. The different polymeric adsorbents can be provided by attaching a precursor molecule to the substrate, initializing the polymerization reaction, and terminating the polymerization reaction at varied degrees of completion for each adsorbent. Also, the terminal functional groups in the polymers can be reacted so as to chemically derivatize them to varying degrees with different affinity reagent (e.g., —NH3, or COO—). By terminating the polymerization or derivatization reaction, adsorbents of varying degrees of polymerization or derivatization are produced. The varying degrees of polymerization or derivatization provide different binding characteristics for each different polymeric adsorbent. This embodiment is particularly useful for providing a plurality of different biopolymer adsorbents on a substrate.

If desired, the polymerization reactions can be carried out in a reaction vessel, rather than on the substrate itself. For example, polymeric adsorbents of varying binding characteristics can be provided by extracting an aliquot of product from the reaction vessel as the polymerization/derivatization reaction is proceeding. The aliquots, having been extracted at various points during the polymerization/derivatization reaction will exhibit varied degrees of polymerization/derivatization to yield a plurality of different adsorbents. The different aliquots of product can then be utilized as adsorbents having different binding characteristics. Alternatively, a plurality of different adsorbents can be provided by sequentially repeating the steps of terminating the reaction, withdrawing an aliquot of product, and re-starting the polymerization/derivatization reaction. The products extracted at each termination point will exhibit varying degrees of polymerization/derivatization and as a result will provide a plurality of adsorbents having different binding characteristics.

In one embodiment, a substrate is provided in the form of a strip or a plate that is coated with adsorbent in which one or more binding characteristic varies in a one- or two-dimensional gradient. For example, a strip is provided having an adsorbent that is weakly hydrophobic at one end and strongly hydrophobic at the other end. Or, a plate is provided that is weakly hydrophobic and anionic in one corner, and strongly hydrophobic and anionic in the diagonally opposite corner. Such adsorption gradients are useful in the qualitative analysis of an analyte. Adsorption gradients can be made by a controlled spray application or by flowing material across a surface in a time-wise manner to allow incremental completion of a reaction over the dimension of the gradient. This process can be repeated, at right angles, to provide orthogonal gradients of similar or different adsorbents with different binding characteristics.

The sample containing the analyte may be contacted to the adsorbent either before or after the adsorbent is positioned on the substrate using any suitable method which will enable binding between the analyte and the adsorbent. The adsorbent can simply be admixed or combined with the sample. The sample can be contacted to the adsorbent by bathing or soaking the substrate in the sample, or dipping the substrate in the sample, or spraying the sample onto the substrate, by washing the sample over the substrate, or by generating the sample or analyte in contact with the adsorbent. In addition, the sample can be contacted to the adsorbent by solubilizing the sample in or admixing the sample with an eluant and contacting the solution of eluant and sample to the adsorbent using any of the foregoing techniques (i.e., bathing, soaking, dipping, spraying, or washing over).

Contacting the analyte to the adsorbent: Exposing the sample to an eluant prior to binding the analyte to the adsorbent has the effect of modifying the selectivity of the adsorbent while simultaneously contacting the sample to the adsorbent. Those components of the sample which will bind to the adsorbent and thereby be retained will include only those components which will bind the adsorbent in the presence of the particular eluant which has been combined with the sample, rather than all components which will bind to the adsorbent in the absence of elution characteristics which modify the selectivity of the adsorbent.

The sample should be contacted to the adsorbent for a period of time sufficient to allow the analyte to bind to the adsorbent. Typically, the sample is contacted with the analyte for a period of between about 30 seconds and about 12 hours. Preferably, the sample is contacted to the analyte for a period of between about 30 seconds and about 15 minutes.

The temperature at which the sample is contacted to the adsorbent is a function of the particular sample and adsorbents selected. Typically, the sample is contacted to the adsorbent under ambient temperature and pressure conditions, however, for some samples, modified temperature (typically 4° C. through 37° C.) and pressure conditions can be desirable and will be readily determinable by those skilled in the art.

Another advantage of the present invention over conventional detection techniques is that the present invention enables the numerous different experiments to be conducted on a very small amount of sample. Generally, a volume of sample containing from a few atommoles to 100 picomoles of analyte in about 1 µl to 500 µl is sufficient for binding to the adsorbent. Analyte may be preserved for future experiments after binding to the adsorbent because any adsorbent locations which are not subjected to the steps of desorbing and detecting all of the retained analyte will retain the analyte thereon. Therefore, in the case where only a very small fraction of sample is available for analysis, the present invention provides the advantage of enabling a multitude of experiments with different adsorbents and/or eluants to be carried out at different times without wasting sample.

Washing the Adsorbent with Eluants: After the sample is contacted with the analyte, resulting in the binding of the analyte to the adsorbent, the adsorbent is washed with eluant. Typically, to provide a multi-dimensional analysis, each adsorbent location is washed with at least a first and a second different eluants. Washing with the eluants modifies the analyte population retained on a specified adsorbent. The combination of the binding characteristics of the adsorbent and the elution characteristics of the eluant provide the selectivity conditions which control the analytes retained by the adsorbent after washing. Thus, the washing step selectively removes sample components from the adsorbent.

The washing step can be carried out using a variety of techniques. For example, as seen above, the sample can be solubilized in or admixed with the first eluant prior to contacting the sample to the adsorbent. Exposing the sample to the first eluant prior to or simultaneously with contacting the sample to the adsorbent has, to a first approximation, the same net effect as binding the analyte to the adsorbent and subsequently washing the adsorbent with the first eluant. After the combined solution is contacted to the adsorbent, the adsorbent can be washed with the second or subsequent eluants.

Washing an adsorbent having the analyte bound thereto can be accomplished by bathing, soaking, or dipping the substrate having the adsorbent and analyte bound thereon in an eluant; or by rinsing, spraying, or washing over the substrate with the eluant. The introduction of eluant to small diameter spots of affinity reagent is best achieved by a microfluidics process.

When the analyte is bound to adsorbent at only one location and a plurality of different eluants are employed in the washing step, information regarding the selectivity of the adsorbent in the presence of each eluant individually may be obtained. The analyte bound to adsorbent at one location may be determined after each washing with eluant by following a repeated pattern of washing with a first eluant, desorbing and detecting retained analyte, followed by washing with a second eluant, and desorbing and detecting retained analyte. The steps of washing followed by desorbing and detecting can be sequentially repeated for a plurality of different eluants using the same adsorbent. In this manner the adsorbent with retained analyte at a single location may be reexamined with a plurality of different eluants to provide a collection of information regarding the analytes retained after each individual washing.

The foregoing method is also useful when adsorbents are provided at a plurality of predetermined addressable locations, whether the adsorbents are all the same or different. However, when the analyte is bound to either the same or different adsorbents at a plurality of locations, the washing step may alternatively be carried out using a more systematic and efficient approach involving parallel processing. Namely, the step of washing can be carried out by washing an adsorbent at a first location with eluant, then washing a second adsorbent with eluant, then desorbing and detecting the analyte retained by the first adsorbent and thereafter desorbing and detecting analyte retained by the second adsorbent. In other words, all of the adsorbents are washed with eluant and thereafter analyte retained by each is desorbed and detected for each location of adsorbent. If desired, after detection at each adsorbent location, a second stage of washings for each adsorbent location may be conducted followed by a second stage of desorption and detection. The steps of washing all adsorbent locations, followed by desorption and detection at each adsorbent location can be repeated for a plurality of different eluants. In this manner, and entire array may be utilized to efficiently determine the character of analytes in a sample. The method is useful whether all adsorbent locations are washed with the same eluant in the first washing stage or whether the plurality of adsorbents are washed with a plurality of different eluants in the first washing stage.

Detection

Analytes retained by the adsorbent after washing are adsorbed to the substrate. Analytes retained on the substrate are detected by desorption spectrometry: desorbing the analyte from the adsorbent and directly detecting the desorbed analytes.

Methods For Desorption: Desorbing the analyte from the adsorbent involves exposing the analyte to an appropriate energy source. Usually this means striking the analyte with radiant energy or energetic particles. For example, the energy can be light energy in the form of laser energy (e.g., UV laser) or energy from a flash lamp. Alternatively, the energy can be a stream of fast atoms. Heat may also be used to induce/aid desorption.

Methods of desorbing and/or ionizing analytes for direct analysis are well known in the art. One such method is called matrix-assisted laser desorption/ionization, or MALDI. In MALDI, the analyte solution is mixed with a matrix solution and the mixture is allowed to crystallize after being deposited on an inert probe surface, trapping the analyte within the crystals may enable desorption. The matrix is selected to absorb the laser energy and apparently impart it to the analyte, resulting in desorption and ionization. Generally, the matrix absorbs in the UV range. MALDI for large proteins is described in, e.g., U.S. Pat. No. 5,118,937 (Hillenkamp et al.) and U.S. Pat. No. 5,045,694 (Beavis and Chait).

Surface-enhanced laser desorption/ionization, or SELDI, represents a significant advance over MALDI in terms of specificity, selectivity and sensitivity. SELDI is described in U.S. Pat. No. 5,719,060 (Hutchens and Yip). SELDI is a solid phase method for desorption in which the analyte is presented to the energy stream on a surface that enhances analyte capture and/or desorption. In contrast, MALDI is a liquid phase method in which the analyte is mixed with a liquid material that crystallizes around the analyte.

One version of SELDI, called SEAC (Surface-Enhanced Affinity Capture), involves presenting the analyte to the desorbing energy in association with an affinity capture device (i.e., an adsorbent). It was found that when an analyte is so adsorbed, it can be presented to the desorbing energy source with a greater opportunity to achieve desorption of the target analyte. An energy absorbing material can be added to the probe to aid desorption. Then the probe is presented to the energy source for desorbing the analyte Another version of SELDI, called SEND (Surface-Enhanced Neat Desorption), involves the use of a layer of energy absorbing material onto which the analyte is placed. A substrate surface comprises a layer of energy absorbing molecules chemically bond to the surface and/or essentially free of crystals. Analyte is then applied alone (i.e., neat) to the surface of the layer, without being substantially mixed with it. The energy absorbing molecules, as do matrix, absorb the desorbing energy and cause the analyte to be desorbed. This improvement is substantial because analytes can now be presented to the energy source in a simpler and more homogeneous manner because the performance of solution mixtures and random crystallization is eliminated. This provides more uniform and predictable results that enable automation of the process. The energy absorbing material can be classical matrix material or can be matrix material whose pH has been neutralized or brought into the basic range. The energy absorbing molecules can be bound to the probe through covalent or noncovalent means.

Another version of SELDI, called SEPAR (Surface-Enhanced Photolabile Attachment and Release), involves the use of photolabile attachment molecules. A photolabile attachment molecule is a divalent molecule having one site covalently bound to a solid phase, such a flat probe surface or another solid phase, such as a bead, that can be made part of the probe, and a second site that can be covalently bound with the affinity reagent or analyte. The photolabile attachment molecule, when bound to both the surface and the analyte, also contains a photolabile bond that can release the affinity reagent or analyte upon exposure to light. The photolabile bond can be within the attachment molecule or at the site of attachment to either the analyte (or affinity reagent) or the probe surface.

Method For Direct Detection Of Analytes: The desorbed analyte can be detected by any of several means. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them.

Alternatively, the analyte can be detectably labeled with, e.g., a fluorescent moiety or with a radioactive moiety. In these cases, the detector can be a fluorescence or radioactivity detector.

A plurality of detection means can be implemented in series to fully interrogate the analyte components and function associated with retentate at each location in the array.

Desorption Detectors: Desorption detectors comprise means for desorbing the analyte from the adsorbent and means for directly detecting the desorbed analyte. That is, the desorption detector detects desorbed analyte without an intermediate step of capturing the analyte in another solid phase and subjecting it to subsequent analysis. Detection of an analyte normally will involve detection of signal strength. This, in turn, reflects the quantity of analyte adsorbed to the adsorbent.

Beyond these two elements, the desorption detector also can have other elements. One such element is means to accelerate the desorbed analyte toward the detector. Another element is means for determining the time-of-flight of analyte from desorption to detection by the detector.

A preferred desorption detector is a laser desorption/ionization mass spectrometer, which is well known in the art. The mass spectrometer includes a port into which the substrate that carries the adsorbed analytes, e.g., a probe, is inserted. Desorption is accomplished by striking the analyte with energy, such as laser energy. The device can include means for translating the surface so that any spot on the array is brought into line with the laser beam. Striking the analyte with the laser results in desorption of the intact analyte into the flight tube and its ionization. The flight tube generally defines a vacuum space. Electrified plates in a portion of the vacuum tube create an electrical potential which accelerate the ionized analyte toward the detector. A clock measures the time of flight and the system electronics determines velocity of the analyte and converts this to mass. As any person skilled in the art understands, any of these elements can be combined with other elements described herein in the assembly of desorption detectors that employ various means of desorption, acceleration, detection, measurement of time, etc.

Selectivity Conditions

One advantage of the invention is the ability to expose the analytes to a variety of different binding and elution conditions, thereby providing both increased resolution of analytes and information about them in the form of a recognition profile. As in conventional chromatographic methods, the ability of the adsorbent to retain the analyte is directly related to the attraction or affinity of the analyte for the adsorbent as compared to the attraction or affinity of the analyte for the eluant or the eluant for the adsorbent. Some components of the sample may have no affinity for the adsorbent and therefore will not bind to the adsorbent when the sample is contacted to the adsorbent. Due to their inability to bind to the adsorbent, these components will be immediately separated from the analyte to be resolved. However, depending upon the nature of the sample and the particular adsorbent utilized, a number of different components can initially bind to the adsorbent.

Adsorbents

Adsorbents are the materials that bind analytes. A plurality of adsorbents can be employed in retentate chromatography. Different adsorbents can exhibit grossly different binding characteristics, somewhat different binding characteristics, or subtly different binding characteristics. Adsorbents which exhibit grossly different binding characteristics typically differ in their bases of attraction or mode of interaction. The basis of attraction is generally a function of chemical or biological molecular recognition. Bases for attraction between an adsorbent and an analyte include, for example, (1) a salt-promoted interaction, e.g., hydrophobic interactions, thiophilic interactions, and immobilized dye interactions; (2) hydrogen bonding and/or van der Waals forces interactions and charge transfer interactions, such as in the case of a hydrophilic interactions; (3) electrostatic interactions, such as an ionic charge interaction, particularly positive or negative ionic charge interactions; (4) the ability of the analyte to form coordinate covalent bonds (i.e., coordination complex formation) with a metal ion on the adsorbent; (5) enzyme-active site binding; (6) reversible covalent interactions, for example, disulfide exchange interactions; (7) glycoprotein interactions; (8) biospecific interactions; or (9) combinations of two or more of the foregoing modes of interaction. That is, the adsorbent can exhibit two or more bases of attraction, and thus be known as a "mixed functionality" adsorbent.

Salt-promoted Interaction Adsorbents: Adsorbents which are useful for observing salt-promoted interactions include hydrophobic interaction adsorbents. Examples of hydrophobic interaction adsorbents include matrices having aliphatic hydrocarbons, specifically C1-C18 aliphatic hydrocarbons; and matrices having aromatic hydrocarbon functional groups such as phenyl groups. Hydrophobic interaction adsorbents bind analytes which include uncharged solvent exposed amino acid residues, and specifically amino acid residues which are commonly referred to as nonpolar, aromatic and hydrophobic amino acid residues, such as phenylalanine and tryptophan. Specific examples of analytes which will bind to a hydrophobic interaction adsorbent include lysozyme and DNA. Without wishing to be bound by a particular theory, it is believed that DNA binds to hydrophobic interaction adsorbents by the aromatic nucleotides in DNA, specifically, the purine and pyrimidine groups.

Another adsorbent useful for observing salt-promoted interactions includes thiophilic interaction adsorbents, such as for example T-GEL® which is one type of thiophilic adsorbent commercially available from Pierce, Rockford, Ill. Thiophilic interaction adsorbents bind, for example, immunoglobulins such as IgG. The mechanism of interaction between IgG and T-GEL® is not completely known, but solvent exposed trp residues are suspected to play a role.

A third adsorbent which involves salt-promoted ionic interactions and also hydrophobic interactions includes immobilized dye interaction adsorbents. Immobilized dye interaction adsorbents include matrices of immobilized dyes such as for example CIBACHRON™ blue available from Pharmacia Biotech, Piscataway, N.J. Immobilized dye interaction adsorbents bind proteins and DNA generally. One specific example of a protein which binds to an immobilized dye interaction adsorbent is bovine serum albumin (BSA).

Hydrophilic Interaction Adsorbents: Adsorbents which are useful for observing hydrogen bonding and/or van der Waals forces on the basis of hydrophilic interactions include surfaces comprising normal phase adsorbents such as silicon-oxide (i.e., glass). The normal phase or silicon-oxide surface, acts as a functional group. In addition, adsorbents comprising surfaces modified with hydrophilic polymers such as polyethylene glycol, dextran, agarose, or cellulose can also function as hydrophilic interaction adsorbents.

Most proteins will bind hydrophilic interaction adsorbents because of a group or combination of amino acid residues (i.e., hydrophilic amino acid residues) that bind through hydrophilic interactions involving hydrogen bonding or van der Waals forces. Examples of proteins which will bind hydrophilic interaction adsorbents include myoglobin, insulin and cytochrome C.

In general, proteins with a high proportion of polar or charged amino acids will be retained on a hydrophilic surface. Alternatively, glycoproteins with surface exposed hydrophilic sugar moieties, also have high affinity for hydrophilic adsorbents.

Electrostatic Interaction Adsorbents: Adsorbents which are useful for observing electrostatic or ionic charge interactions include anionic adsorbents such as, for example, matrices of sulfate anions (i.e., SO3-) and matrices of carboxylate anions (i.e., COO—) or phosphate anions (OPO3-). Matrices having sulfate anions are permanent negatively charged. However, matrices having carboxylate anions have a negative charge only at a pH above their pKa. At a pH below the pKa, the matrices exhibit a substantially neutral charge. Suitable anionic adsorbents also include anionic adsorbents which are matrices having a combination of sulfate and carboxylate anions and phosphate anions. The combination provides an intensity of negative charge that can be continuously varied as a function of pH. These adsorbents attract and bind proteins and macromolecules having positive charges, such as for example ribonuclease and lactoferrin. Without wishing to be bound by a particular theory, it is believed that the electrostatic interaction between an adsorbent and positively charged amino acid residues including lysine residues, arginine residues, and histidyl residues are responsible for the binding interaction.

Other adsorbents which are useful for observing electrostatic or ionic charge interactions include cationic adsorbents. Specific examples of cationic adsorbents include matrices of secondary, tertiary or quaternary amines. Quaternary amines are permanently positively charged. However, secondary and tertiary amines have charges that are pH dependent. At a pH below the pKa, secondary and tertiary amines are positively charged, and at a pH above their pKa, they are negatively charged. Suitable cationic adsorbents also include cationic adsorbents which are matrices having combinations of different secondary, tertiary, and quaternary amines. The combination provides an intensity of positive charge that can be continuously varied as a function of pH. Cationic interaction adsorbents bind anionic sites on molecules including proteins having solvent exposed amino acid residues, such as aspartic acid and glutamic acid residues.

In the case of ionic interaction adsorbents (both anionic and cationic) it is often desirable to use a mixed mode ionic adsorbent containing both anions and cations. Such adsorbents provide a continuous buffering capacity as a function of pH. The continuous buffering capacity enables the exposure of a combination of analytes to eluants having differing buffering components especially in the pH range of from 2 to 11. This results in the generation of local pH environments on the adsorbent which are defined by immobilized titratable proton exchange groups. Such systems are equivalent to the solid phase separation technique known as chromatofocusing. Follicle stimulating hormone isoforms, which differ mainly in the charged carbohydrate components are separated on a chromatofocusing adsorbent.

Still other adsorbents which are useful for observing electrostatic interactions include dipole-dipole interaction adsorbents in which the interactions are electrostatic but no formal charge or titratable protein donor or acceptor is involved.

Coordinate Covalent Interaction Adsorbents: Adsorbents which are useful for observing the ability to form coordinate covalent bonds with metal ions include matrices bearing, for example, divalent and trivalent metal ions. Matrices of immobilized metal ion chelators provide immobilized synthetic organic molecules that have one or more electron donor groups which form the basis of coordinate covalent interactions with transition metal ions. The primary electron donor groups functioning as immobilized metal ion chelators include oxygen, nitrogen, and sulfur. The metal ions are bound to the immobilized metal ion chelators resulting in a metal ion complex having some number of remaining sites for interaction with electron donor groups on the analyte. Suitable metal ions include in general transition metal ions such as copper, nickel, cobalt, zinc, iron, and other metal ions such as aluminum and calcium. Without wishing to be bound by any particular theory, metals ions are believed to interact selectively with specific amino acid residues in peptides, proteins, or nucleic acids. Typically, the amino acid residues involved in such interactions include histidine residues, tyrosine residues, tryptophan residues, cysteine residues, and amino acid residues having oxygen groups such as aspartic acid and glutamic acid. For example, immobilized ferric ions interact with phosphoserine, phosphotyrosine, and phosphothreonine residues on proteins. Depending on the immobilized metal ion, only those proteins with sufficient local densities of the foregoing amino acid residues will be retained by the adsorbent. Some interactions between metal ions and proteins can be so strong that the protein cannot be severed from the complex by conventional means. Human β casein, which is highly phosphorylated, binds very strongly to immobilized Fe(III). Recombinant proteins which are expressed with a 6-Histidine tag, binds very strongly to immobilized Cu(II) and Ni(II).

Enzyme-Active Site Interaction Adsorbents: Adsorbents which are useful for observing enzyme-active site binding interactions include proteases (such as trypsin), phosphatases, kinases, and nucleases. The interaction is a sequence-specific interaction of the enzyme binding site on the analyte (typically a biopolymer) with the catalytic binding site on the enzyme. Enzyme binding sites of this type include, for example, active sites of trypsin interacting with proteins and peptides having lysine-lysine or lysine-arginine pairs in their sequence. More specifically, soybean trypsin inhibitor interacts with and binds to an adsorbent of immobilized trypsin. Alternatively, serine proteases are selectively retained on immobilized L-arginine adsorbent.

Reversible Covalent Interaction Adsorbents: Adsorbents which are useful for observing reversible covalent interactions include disulfide exchange interaction adsorbents. Disulfide exchange interaction adsorbents include adsorbents comprising immobilized sulfhydryl groups, e.g., mercaptoethanol or immobilized dithiothrietol. The interaction is based upon the formation of covalent disulfide bonds between the adsorbent and solvent exposed cysteine residues on the analyte. Such adsorbents bind proteins or peptides having cysteine residues and nucleic acids including bases modified to contain reduced sulfur compounds.

Glycoprotein Interaction Adsorbents: Adsorbents which are useful for observing glycoprotein interactions include glycoprotein interaction adsorbents such as adsorbents having immobilize lectins (i.e., proteins bearing oligosaccharides) therein, an example of which is CONCONAVALIN™, which is commercially available from Pharmacia Biotech of Piscataway, N.J. Such adsorbents function on the basis of the interaction involving molecular recognition of carbohydrate moieties on macromolecules. Examples of analytes which interact with and bind to glycoprotein interaction adsorbents include glycoproteins, particularly histidine-rich glycoproteins, whole cells and isolated subcellular fractions.

Biospecific Interaction Adsorbent: Adsorbents which are useful for observing biospecific interactions are generically termed "biospecific affinity adsorbents." Adsorption is considered biospecific if it is selective and the affinity (equilibrium dissociation constant, Kd) is at least 10-3 M to (e.g., 10-5 M, 10-7 M, 10-9 M). Examples of biospecific affinity adsorbents include any adsorbent which specifically interacts with and binds a particular biomolecule. Biospecific affinity adsorbents include for example, immobilized antibodies which bind to antigens; immobilized DNA which binds to DNA binding proteins, DNA, and RNA; immobilized substrates or inhibitors which bind to proteins and enzymes; immobilized drugs which bind to drug binding proteins; immobilized ligands which bind to receptors; immobilized receptors which bind to ligands; immobilized RNA which binds to DNA and RNA binding proteins; immobilized avidin or streptavidin which bind biotin and biotinylated molecules; immobilized phospholipid membranes and vesicles which bind lipid-binding proteins. Enzymes are useful adsorbents that can modify an analyte adsorbent thereto. Cells are useful as adsorbents. Their surfaces present complex binding characteristics. Adsorption to cells is useful for identifying, e.g., ligands or signal molecules that bind to surface receptors. Viruses or phage also are useful as adsorbents. Viruses frequently have ligands for cell surface receptors (e.g., gp120 for CD4). Also, in the form a phage display library, phage coat proteins act as agents for testing binding to targets. Biospecific interaction adsorbents rely on known specific interactions such as those described above. Other examples of biospecific interactions for which adsorbents can be utilized will be readily apparent to those skilled in the art and are contemplated by the present invention.

In one embodiment, the biospecific adsorbent can further comprise an auxiliary, or "helper", molecule that does not directly participate in binding the target analyte.

Degrees of Binding Specificity: By exposure to adsorbents having different modes of interaction, the components of a sample can be grossly divided based upon their interaction with the different adsorbents. Thus, the attraction of the analyte for adsorbents having different modes of interaction provides a first separation parameter. For example, by exposing a sample containing the analyte to a first adsorbent with a basis of attraction involving hydrophobicity and a second adsorbent with a basis of attraction involving ionic charge, it is possible to separate from the sample those analytes which bind to a hydrophobic adsorbent and to separate those analytes which bind to an adsorbent having the particular ionic charge.

Adsorbents having different bases of attraction provide resolution of the analyte with a low degree of specificity because the adsorbent will bind not only the analyte, but any other component in the sample which also exhibits an attraction for the adsorbent by the same basis of attraction. For example, a hydrophobic adsorbent will bind not only a hydrophobic analyte, but also any other hydrophobic components in the sample; a negatively charged adsorbent will bind not only a positively charged analyte, but also any other positively charged component in the sample; and so on.

The resolution of analytes based upon the basis of attraction of the analyte for the adsorbent can be further refined by exploiting binding characteristics of relatively intermediate specificity or altered strength of attraction. Resolution of the analyte on the basis of binding characteristics of intermediate specificity can be accomplished, for example, by utilizing mixed functionality adsorbents. Once the resolution of the analyte is accomplished with relatively low specificity, the binding characteristic found to attract the analyte of interest can be exploited in combination with a variety of other binding and elution characteristics to remove still more undesired components and thereby resolve the analyte.

For example, if the analyte binds to hydrophobic adsorbents, the analyte can be further resolved from other hydrophobic sample components by providing a mixed functionality adsorbent which exhibits as one basis of attraction a hydrophobic interaction and also exhibits a second, different basis of attraction. The mixed functionality adsorbent may exhibit hydrophobic interactions and negatively charged ionic interactions so as to bind hydrophobic analytes which are positively charged. Alternatively, the mixed functionality adsorbent can exhibit hydrophobic interactions and the ability to form coordinate covalent bonds with metal ions so as to bind hydrophobic analytes having the ability to form coordination complexes with metal ions on the adsorbent. Still further examples of adsorbents exhibiting binding characteristics of intermediate specificity will be readily apparent to those skilled in the art based upon the disclosure and examples set forth above.

The resolution of analytes on the basis of binding characteristics of intermediate specificity can be further refined by exploiting binding characteristics of relatively high specificity. Binding characteristics of relatively high specificity can be exploited by utilizing a variety of adsorbents exhibiting the same basis of attraction but a different strength of attraction. In other words, although the basis of attraction is the same, further resolution of the analyte from other sample components can be achieved by utilizing adsorbents having different degrees of affinity for the analyte.

For example, an analyte that binds an adsorbent based upon the analyte's acidic nature may be further resolved from other acidic sample components by utilizing adsorbents having affinity for analytes in specific acidic pH ranges. Thus the analyte may be resolved using one adsorbent attracted to sample components of pH 1-2, another adsorbent attracted to sample components of pH of 3-4, and a third adsorbent attracted to sample components of pH of 5-6. In this manner, an analyte having a specific affinity for an adsorbent which binds analyte of pH of 5-6 will be resolved from sample components of pH of 1-4. Adsorbents of increasing specificity can be utilized by decreasing the interval of attraction, i.e., the difference between the binding characteristics of adsorbents exhibiting the same basis of attraction.

A primary analyte adsorbed to a primary adsorbent can, itself, have adsorbent properties. In this case, the primary analyte adsorbed to a substrate can become a secondary adsorbent for isolating secondary analytes. In turn, the retained secondary analyte can function as a tertiary adsorbent to isolate a tertiary analyte from a sample. This process can continue through several iterations.

Eluants

The eluants, or wash solutions, selectively modify the threshold of absorption between the analyte and the adsorbent. The ability of an eluant to desorb and elute a bound analyte is a function of its elution characteristics. Different eluants can exhibit grossly different elution characteristics, somewhat different elution characteristics, or subtly different elution characteristics.

The temperature at which the eluant is contacted to the adsorbent is a function of the particular sample and adsorbents selected. Typically, the eluant is contacted to the adsorbent at a temperature of between 0° C. and 100° C., preferably between 4° C. and 37° C. However, for some eluants, modified temperatures can be desirable and will be readily determinable by those skilled in the art.

As in the case of adsorbents, eluants which exhibit grossly different elution characteristics generally differ in their basis of attraction. For example, various bases of attraction between the eluant and the analyte include charge or pH, ionic strength, water structure, concentrations of specific competitive binding reagents, surface tension, dielectric constant and combinations of two or more of the above.

pH-Based Eluants: Eluants which modify the selectivity of the adsorbent based upon pH (i.e., charge) include known pH buffers, acidic solutions, and basic solutions. By washing an analyte bound to a given adsorbent with a particular pH buffer, the charge can be modified and therefore the strength of the bond between the adsorbent and the analyte in the presence of the particular pH buffer can be challenged. Those analytes which are less competitive than others for the adsorbent at the pH of the eluant will be desorbed from the adsorbent and eluted, leaving bound only those analytes which bind more strongly to the adsorbent at the pH of the eluant.

Ionic Strength-Based Eluants: Eluants which modify the selectivity of the adsorbent with respect to ionic strength include salt solutions of various types and concentrations. The amount of salt solubilized in the eluant solution affects the ionic strength of the eluant and modifies the adsorbent binding ability correspondingly. Eluants containing a low concentration of salt provide a slight modification of the adsorbent binding ability with respect to ionic strength. Eluants containing a high concentration of salt provide a greater modification of the adsorbent binding ability with respect to ionic strength.

Water Structure-Based Eluants: Eluants which modify the selectivity of the adsorbent by alteration of water structure or concentration include urea and chaotropic salt solutions. Typically, urea solutions include, e.g., solutions ranging in concentration from 0.1 to 8 M. Chaotropic salts which can be used to provide eluants include sodium thiocyanate. Water structure-based eluants modify the ability of the adsorbent to bind the analyte due to alterations in hydration or bound water structure. Eluants of this type include for example, glycerol, ethylene glycol and organic solvents. Chaotropic anions increase the water solubility of nonpolar moieties thereby decreasing hydrophobic interactions between the analyte and the adsorbent.

Detergent-Based Eluants: Eluants which modify the selectivity of the adsorbent with respect to surface tension and analyte structure include detergents and surfactants. Suitable detergents for use as eluants include ionic and nonionic detergents such as CHAPS, TWEEN and NP-40. Detergent-based eluants modify the ability of the adsorbent to bind the analyte as the hydrophobic interactions are modified when the hydrophobic and hydrophilic groups of the detergent are introduced. Hydrophobic interactions between the analyte and the adsorbent, and within the analyte are modified and charge groups are introduced, e.g., protein denaturation with ionic detergents such as SDS.

Hydrophobicity-Based Eluants: Eluants which modify the selectivity of the adsorbent with respect to dielectric constant are those eluants which modify the selectivity of the adsorbent with respect to hydrophobic interaction. Examples of suitable eluants which function in this capacity include urea (0.1-8M) organic solvents such as propanol, acetonitrile, ethylene glycol and glycerol, and detergents such as those mentioned above. Use of acetonitrile as eluant is typical in reverse phase chromatography. Inclusion of ethylene glycol in the eluant is effective in eluting immunoglobulins from salt-promoted interactions with thiophilic adsorbents.

Combinations of Eluants: Suitable eluants can be selected from any of the foregoing categories or can be combinations of two or more of the foregoing eluants. Eluants which comprise two or more of the foregoing eluants are capable of modifying the selectivity of the adsorbent for the analyte on the basis of multiple elution characteristics.

Variability of Two Parameters

The ability to provide different binding characteristics by selecting different adsorbents and the ability to provide different elution characteristics by washing with different eluants permits variance of two distinct parameters each of which is capable of individually effecting the selectivity with which analytes are bound to the adsorbent. The fact that these two parameters can be varied widely assures a broad range of binding attraction and elution conditions so that the methods of the present invention can be useful for binding and thus detecting many different types of analytes.

The selection of adsorbents and eluants for use in analyzing a particular sample will depend on the nature of the sample, and the particular analyte or class of analytes to be characterized, even if the nature of the analytes are not known. Typically, it is advantageous to provide a system exhibiting a wide variety of binding characteristics and a wide variety of elution characteristics, particularly when the composition of the sample to be analyzed is unknown. By providing a system exhibiting broad ranges of selectivity characteristics, the likelihood that the analyte of interest will be retained by one or more of the adsorbents is significantly increased.

One skilled in the art of chemical or biochemical analysis is capable of determining the selectivity conditions useful for retaining a particular analyte by providing a system exhibiting a broad range of binding and elution characteristics and observing binding and elution characteristics which provide the best resolution of the analyte. Because the present invention provides for systems including broad ranges of selectivity conditions, the determination by one skilled in the art of the optimum binding and elution characteristics for a given analyte can be easily accomplished without the need for undue experimentation.

Analytes

The present invention permits the resolution of analytes based upon a variety of biological, chemical, or physiochemical properties of the analyte by exploiting the properties of the analyte through the use of appropriate selectivity conditions. Among the many properties of analytes which can be exploited through the use of appropriate selectivity conditions are the hydrophobic index (or measure of hydrophobic residues in the analyte), the isoelectric point (i.e., the pH at which the analyte has no charge), the hydrophobic moment (or measure of amphipathicity of an analyte or the extent of asymmetry in the distribution of polar and nonpolar residues), the lateral dipole moment (or measure of asymmetry in the distribution of charge in the analyte), a molecular structure factor (accounting for the variation in surface contour of the analyte molecule such as the distribution of bulky side chains along the backbone of the molecule), secondary structure components (e.g., helix, parallel and antiparallel sheets), disulfide bands, solvent-exposed electron donor groups (e.g., His), aromaticity (or measure of pi-pi interaction among aromatic residues in the analyte) and the linear distance between charged atoms.

These are representative examples of the types of properties which can be exploited for the resolution of a given analyte from a sample by the selection of appropriate selectivity characteristics in the methods of the present invention. Other suitable properties of analytes which can form the basis for resolution of a particular analyte from the sample will be readily known and/or determinable by those skilled in the art and are contemplated by the instant invention.

The inventive method is not limited with respect to the types of samples which can be analyzed. Samples can be in the solid, liquid, or gaseous state, although typically the sample will be in a liquid state. Solid or gaseous samples are preferably solubilized in a suitable solvent to provide a liquid sample according to techniques well within the skill of those in the art. The sample can be a biological composition, non-biological organic composition, or inorganic composition. The technique of the present invention is particularly useful for resolving analytes in a biological sample, particularly biological fluids and extracts; and for resolving analytes in non-biological organic compositions, particularly compositions of small organic and inorganic molecules.

The analytes may be molecules, multimeric molecular complexes, macromolecular assemblies, cells, subcellular organelles, viruses, molecular fragments, ions, or atoms. The analyte can be a single component of the sample or a class of structurally, chemically, biologically, or finctionally related components having one or more characteristics (e.g., molecular weight, isoelectric point, ionic charge, hydrophobic/hydrophilic interaction, etc.) in common.

Specific examples of analytes which may be resolved using the retentate chromatography methods of the present invention include biological macromolecules such as peptides, proteins, enzymes, polynucleotides, oligonucleotides, nucleic acids, carbohydrates, oligosaccharides, polysaccharides; fragments of biological macromolecules set forth above, such as nucleic acid fragments, peptide fragments, and protein fragments; complexes of biological macromolecules set forth above, such as nucleic acid complexes, protein-DNA complexes, receptor-ligand complexes, enzyme-substrate, enzyme inhibitors, peptide complexes, protein complexes, carbohydrate complexes, and polysaccharide complexes; small biological molecules such as amino acids, nucleotides, nucleosides, sugars, steroids, lipids, metal ions, drugs, hormones, amides, amines, carboxylic acids, vitamins and coenzymes, alcohols, aldehydes, ketones, fatty acids, porphyrins, carotenoids, plant growth regulators, phosphate esters and nucleoside diphospho-sugars, synthetic small molecules such as pharmaceutically or therapeutically effective agents, monomers, peptide analogs, steroid analogs, inhibitors, mutagens, carcinogens, antimitotic drugs, antibiotics, ionophores, antimetabolites, amino acid analogs, antibacterial agents, transport inhibitors, surface-active agents (surfactants), mitochondrial and chloroplast function inhibitors, electron donors, carriers and acceptors, synthetic substrates for proteases, substrates for phosphatases, substrates for esterases and lipases and protein modification reagents; and synthetic polymers, oligomers, and copolymers such as polyalkylenes, polyamides, poly(meth)acrylates, polysulfones, polystyrenes, polyethers, polyvinyl ethers, polyvinyl esters, polycarbonates, polyvinyl halides, polysiloxanes, POMA, PEG, and copolymers of any two or more of the above.

Identifying the Polypeptide Encoded by the mRNA

Once the polypeptides are fractionated, a next step is identifying a polypeptide from among the fractionated polypeptides that corresponds to the polypeptide encoded by the selected mRNA. The polypeptides in the sample have been fractionated based on a known physio-chemical property of the encoded polypeptide. This information is useful in discovering the encoded polypeptide from among the fractionated polypeptides. For example, one may know that an encoded polypeptide has a negative charge at pH 7 and a mass of about 18 kD. Using a protein biochip comprising an anionic adsorbent spot, one could capture proteins having a negative charge at pH 7. Then, using a mass spectrometer, the captured proteins are fractionated based on molecular weight, providing a spectrum. Examining the spectrum at around 18 kD will provide one or more candidate proteins having the selected physiochemical properties. The candidates can now be examined further by a variety of methods described herein to determine their identity and correlated them with the expressed polypeptide.

Similarly, two-dimensional gel electrophoresis separates proteins based on pI and molecular weight. Knowing the predicted mass and pI of the expressed protein leads the investigator to a particular region of the gel expected to comprise the protein. The proteins in that spot are then examined to correlated them to the expressed protein using, e.g., tandem mass spectrometric analysis coupled with interrogation of a protein database.

Identification of Proteins Fractionated by Mass Spectrometry

The data of a mass spectrum can be used to identify the proteins present in a sample by executing an algorithm with a programmable digital computer that compares the MS data to records in a database. Each molecule provides characteristic mass-spectrometric (MS) data (also referred to as a mass spectral "signature" or "fingerprint") when analyzed by MS methods. This data can be analyzed by comparing it to databases containing, inter alia, actual or theoretical MS data or biopolymer sequence information. Additionally, a molecule may be cleaved into fragments for MS analysis. Information obtained from the MS analysis of fragments is also compared to a database to identify polypeptides in the analyte (Yates, *J. Mass Spec.* 33: 1-19 (1988); Yates et al., U.S. Pat. No. 5,538,897; Yates et al., U.S. Pat. No. 6,017, 693).

Further methods for identifying proteins detected by SELDI are described, e.g., in U.S. Pat. No. 6,225,047; International Patent Application PCT/US00/28163, and U.S. Ser. No. 60/277,677, filed Mar. 20, 2001.

Data generated by desorption and detection of polypeptides can be analyzed using any suitable means. In one embodiment, data is analyzed with the use of a programmable digital computer. The computer program generally contains a readable medium that stores codes. Certain code can be devoted to memory that includes the location of each feature on a substrate, the identity of the adsorbent at that feature and the elution conditions used to wash the adsorbent. Using this information, the program can then identify the set of features on the substrate defining certain selectivity characteristics (e.g., types of adsorbent and eluants used).

The computer also contains code that receives as input, data on the strength of the signal at various molecular masses received from a particular addressable location on the substrate. This data can indicate the number of polypeptides detected, optionally including the strength of the signal and the determined molecular mass for each polypeptide detected.

Data analysis can include the steps of determining signal strength (e.g., height of peaks) of a polypeptide detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each polypeptide or other substances can be displayed in the form of relative intensities in the scale desired (e.g., 100). Alternatively, a standard may be admitted with the sample so that a peak from the standard can be used as a reference to calculate relative intensities of the signals observed for each polypeptide or other polypeptides detected.

In certain embodiments, MS data and information obtained from that data are compared to a database consisting of data and information relating to biopolymers. For example, the database may consist of sequences of nucleotides or amino acids. The database may consist of nucleotide or amino acid sequences of expressed sequence tags (ESTs). Alternatively, the database may consist of sequences of genes at the nucleotide or amino acid level. The database can include, without limitation, a collection of nucleotide sequences, amino acid sequences, or translations of nucleotide sequences included in the genome of any species.

A database of information relating to biopolymers, e.g., sequences of nucleotides or amino acids, is typically analyzed via a computer program or a search algorithm which is optionally performed by a computer. Information from sequence databases is searched for best matches with data and information obtained from the methods of the present invention (see e.g., Yates (1998) *J. Mass Spec.* 33: 1-19; Yates et al., U.S. Pat. No. 5,538,897; Yates et al., U.S. Pat. No. 6,017,693).

Any appropriate algorithm or computer program useful for searching a database can be used. Search algorithms and databases are constantly updated, and such updated versions will be used in accordance, with the present invention. U.S. Pat. Nos. 5,632,041; 5,964,860; 5,706,498; and 5,701,256 also describe algorithms or methods for sequence comparison.

In one embodiment, the database of protein, peptide, or nucleotide sequences is a combination of databases. Examples of databases include, but are not limited to, ProteinProspector at the UCSF web site (prospector.ucsf.edu), the Genpept database, the GenBank database (described in Burks et al. (1990) *Methods in Enzymology* 183: 3-22, EMBL data library (described in Kahn et al. (1990) *Methods in Enzymology* 183:23-31, the Protein Sequence Database (described in Barker et al. (1990) *Methods in Enzymology* 183: 31-49, SWISS-PROT (described in Bairoch et al. (1993) *Nucleic Acids Res.*, 21: 3093-3096, and PIR-International (described in (1993) *Protein Seg. Data Anal.* 5:67-192).

In a further embodiment, novel databases are generated for comparison to mass spectrometrically determined MS data, e.g., mass or mass spectra of cleaved protein and peptide fragments. For example, a theoretical database of all the possible amino acid sequence combinations of the peptide masses being characterized is generated (Parekh et al., WO 98/53323). Then, the database is compared with the actual masses determined using mass spectrometry to determine the amino acid sequence of the peptides in the sample.

In some embodiments, the mass of a polypeptide derived from a mass spectrum is used to query a database for those masses of proteins or predicted proteins from nucleic acid sequences that provide the closest fit. In this manner, an unknown protein can be rapidly identified without an amino acid sequence. In other embodiments of the invention, the masses provided from chimeric polypeptide fragments thereof can be compared to the predicted mass spectra of a database of proteins or predicted proteins from a nucleic acid sequences that provide the closest fit. An algorithm or computer program generates a theoretical cleavage of sequences in a database with the same cleavage agent used to cleave the biopolymer analyzed by MS methods.

Sequences or simulated cleavage fragments from the sequence database that fall within a desired range of similar sequence homologies to sequences generated from the MS data of parent or fragment molecules are designated "matches" or "hits." In this manner, the identity of the test domain or fragments thereof can be rapidly determined. The investigator can customize or vary the range of acceptable sequence homology comparison values according to each particular analysis.

Detection of Polypeptides Using SELDI

Detection of analytes adsorbed to an adsorbent under particular elution conditions provides information about analytes in a sample and their chemical character. Adsorption depends, in part, upon the binding characteristics of the adsorbent: Analytes that bind to an adsorbent possess the characteristic that makes binding possible. For example, molecules that are cationic at a particular pH will bind to an anionic adsorbent under elution conditions that include that pH. Strongly cationic molecules will only be eluted from the adsorbent under very strong elution conditions. Molecules with hydrophobic regions will bind to hydrophobic adsorbents, while molecules with hydrophilic regions will bind to hydrophilic adsorbents. Again, the strength of the interaction will depend, in part, upon extent to which an analyte contains hydrophobic or hydrophilic regions. Thus, the determination that certain analytes in a sample bind to an adsorbent under certain elution conditions not only resolves analytes in a mixture by separating them from each other and from analytes that do not possess the appropriate chemical character for binding, but also identifies a class of analytes or individual analytes having the particular chemical character. Collecting information about analyte retention on one or more particular adsorbents under a variety of elution conditions provides not only detailed resolution of analytes in a mixture, but also chemical information about the analytes, themselves that can lead to their identity. This data is referred to as "retention data."

Data generated in retention assays is most easily analyzed with the use of a programmable digital computer. The computer program generally contains a readable medium that stores codes. Certain code is devoted to memory that includes the location of each feature on a substrate array, the identity of the adsorbent at that feature and the elution conditions used to wash the adsorbent. Using this information, the program can then identify the set of features on the array defining certain selectivity characteristics. The computer also contains code that receives as input, data on the strength of the signal at various molecular masses received from a particular addressable location on the probe. This data can indicate the number of analytes detected, optionally including for each analyte detected the strength of the signal and the determined molecular mass.

The computer also contains code that processes the data. This invention contemplates a variety of methods for processing the data. In one embodiment, this involves creating an analyte recognition profile. For example, data on the retention of a particular analyte identified by molecular mass can be sorted according to a particular binding characteristic, for example, binding to anionic adsorbents or hydrophobic adsorbents. This collected data provides a profile of the chemical properties of the particular analyte. Retention characteristics reflect analyte function which, in turn, reflects structure. For example, retention to coordinate covalent metal chelators can reflect the presence of histidine residues in a polypeptide analyte. Using data of the level of retention to a plurality of cationic and anionic adsorbents under elution at a variety of pH levels reveals information from which one can derive the isoelectric point of a protein. This, in turn, reflects the probable number of ionic amino acids in the protein. Accordingly, the computer can include code that transforms the binding information into structural information. Furthermore, secondary processing of the analyte (e.g., post-translational modifications) results in an altered recognition profile reflected by differences in binding or mass.

In another embodiment, retention assays are performed under the same set of selectivity thresholds on two different cell types, and the retention data from the two assays is compared. Differences in the retention maps (e.g., presence or strength of signal at any feature) indicate analytes that are differentially expressed by the two cells. This can include, for example, generating a difference map indicating the difference in signal strength between two retention assays, thereby indicating which analytes are increasingly or decreasingly retained by the adsorbent in the two assays.

The computer program also can include code that receives instructions from a programmer as input. The progressive and logical pathway for selective desorption of analytes from specified, predetermined locations in the array can be anticipated and programmed in advance.

The computer can transform the data into another format for presentation. Data analysis can include the steps of determining, e.g., signal strength as a function of feature position from the data collected, removing "outliers" (data deviating from a predetermined statistical distribution), and calculating the relative binding affinity of the analytes from the remaining data.

The resulting data can be displayed in a variety of formats. In one format, the strength of a signal is displayed on a graph as a function of molecular mass. In another format, referred to as "gel format," the strength of a signal is displayed along a linear axis intensity of darkness, resulting in an appearance similar to bands on a gel. In another format, signals reaching a certain threshold are presented as vertical lines or bars on a horizontal axis representing molecular mass. Accordingly, each bar represents an analyte detected. Data also can be presented in graphs of signal strength for an analyte grouped according to binding characteristic and/or elution characteristic.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of correlating gene expression with protein expression in two or more biological samples, the method comprising the steps of:
   a) obtaining two or more biological samples;
   b) generating a gene expression profile of each sample;
   c) determining the nucleotide sequence of at least one mRNA in each gene expression profile;
   d) predicting the amino acid sequence of the polypeptide encoded by the at least one mRNA in each gene expression profile;
   e) predicting the mass of the polypeptide encoded by the at least one mRNA in each gene expression profile;
   f) generating a protein profile of polypeptides in each sample by mass spectrometry; and
   g) determining the presence in each protein profile of a polypeptide having a mass that is the same as the predicted mass of the encoded polypeptide, thereby identifying at least one protein that is expressed from a corresponding mRNA in each biological sample, thereby correlating gene expression with protein expression in two or more biological samples.

2. The method of claim 1, wherein one of the biological samples comprises a cell lysate from a healthy cell.

3. The method of claim 1, wherein one of the biological samples comprises a cell lysate from a pathological cell.

4. The method of claim 1, wherein one of the biological samples comprises a cell lysate from a cell contacted by a toxic compound.

5. The method of claim 1, wherein one of the biological samples comprises a cell lysate from a cell of a subject who responds to a drug treatment 6. The method of claim 1, wherein one of the biological samples comprises a cell lysate from a cell of a subjcot who does not respond to a drug treatment.

7. The method of claim 1, wherein the biological samples comprise human cells.

8. The method of claim 1, wherein the step of generating the gene expression profile comprises identifying expressed mRNA with a nucleic acid array.

9. The method of claim 1, wherein the step of generating the gene expression profile comprises identifying expressed mRNA with an oligonucleotide array.

10. The method of claim 1, wherein the step of generating the gene expression profile comprises identifying expressed mRNA with an mRNA array.

11. The method of claim 1, wherein the step of generating the gene expression profile comprises identifying expressed mRNA with an EST array.

12. The method of claim 1, wherein the step of generating the gene expression profile comprises identifying expressed mRNA with a northern blot or a dot blot.

13. The method of claim 1, wherein two biological samples are derived from a normal cell and a pathologic cell.

14. The method of claim 13, wherein the pathologic cell is a cancer cell.

15. The method of claim 1, wherein two biological samples are derived from a healthy cell and a cell exposed to a toxic compound.

16. The method of claim 1, wherein mass spectrometry is laser desorption/ionization mass spectrometry.

17. The method of claim 1, wherein mass spectrometry is electrospray mass spectrometry.

18. The method of claim 1, further comprising,
   in step d), after predicting the amino acid sequence of the polypeptide encoded by the at least one mRNA in each gene expression profile, predicting a post-translational modification of the encoded polypeptide;

in step e), after predicting the mass of the polypeptide encoded by the at least one mRNA in each gene expression profile, predicting the mass of the encoded polypeptide to reflect the post-translational modification; and in step g), after determining the presence in each protein profile of a polypeptide having a mass that correlates to the predicted mass of the encoded polypeptide, determining the presence of a polypeptide having a mass that correlates to the predicted mass of the encoded polypeptide having the post-translational modification.

19. The method of claim 18, wherein the post-translational modification is phosphorylation or glycosylation.

20. The method of claim 1 further comprising:
(i) after step d), predicting at least one physio-chemical characteristic of the polypeptide encoded by the at least one mRNA in each gene expression profile selected from the group consisting of isoelectric point, hydrophobicity, hydrophilicity, glycosylation, phosphorylation, epitope sequence, ligand binding sequence, and metal chelate binding;
(ii) fractionating the polypeptides in each sample according to the at least one physiochemical characteristic, retaining the fraction containing the predicted physiochemical property, and then generating a protein profile of polypeptides in each sample by mass spectrometry in step f); and
(iii) in step g), correlating the predicted mass and the at least one physiochemical characteristic of each polypeptide encoded by the at least one mRNA in each gene expression profile with a polypeptide in each respective protein expression profile.

21. The method of claim 20, wherein the physio-chemical characteristic is isoelectric point and fractionating the polypeptides comprises isoelectric focusing.

22. The method of claim 20, wherein the physiochemical characteristic is isoelectric point and fractionating the polypeptides comprises capturing polypeptides on a solid phase-bound ion exchange adsorbent, washing away unbound polypeptides and detecting the bound polypeptides by laser desoprtion/ionization mass spectrometry.

23. The method of claim 20, wherein the physiochemical characteristic is hydrophobicity and fractionating the polypeptides comprises capturing polypeptides on a solid phase-bound hydrophobic interaction adsorbent, washing away unbound polypeptides and detecting the bound polypeptides by laser desoprtion/ionization mass spectrometry.

24. The method of claim 20, wherein the physiochemical characteristic is hydrophilicity and fractionating the polypeptides comprises capturing polypeptides on a solid phase-bound hydrophilic interaction adsorbent, washing away unbound polypeptides and detecting the bound polypeptides by laser desoprtion/ionization mass spectrometry.

25. The method of claim 20, wherein the physiochemical characteristic is epitope sequence and fractionating the polypeptides comprises capturing polypeptides on a solid phase-bound biospecific adsorbent, washing away unbound polypeptides and detecting the bound polypeptides by laser desoprtion/ionization mass spectrometry.

26. The method of claim 20, wherein the physiochemical characteristic is metal chelate binding and fractionating the polypeptides comprises capturing polypeptides on a solid phase-bound immobilized metal chelate adsorbent, washing away unbound polypeptides and detecting the bound polypeptides by laser desoprtion/ionization mass spectrometry.

* * * * *